United States Patent [19]

Smith et al.

[11] Patent Number: 5,849,966
[45] Date of Patent: *Dec. 15, 1998

[54] CATALYST AND PROCESS FOR THE ISOMERIZATION OF OLEFINS IN THE PRESENCE OF REACTIVE IMPURITIES

[75] Inventors: Robert Scott Smith, Houston, Tex.; Christopher Lynn Becker, Baton Rouge, La.

[73] Assignee: Exxon Chemical Patents Inc., Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 475,957

[22] Filed: Jun. 7, 1995

Related U.S. Application Data

[63] Continuation-in-part of Ser. No. 405,650, Mar. 17, 1995, abandoned, which is a continuation-in-part of Ser. No. 150,946, Nov. 12, 1993, abandoned, which is a continuation-in-part of Ser. No. 775,776, Oct. 11, 1991, abandoned, which is a continuation-in-part of Ser. No. 700,016, May 14, 1991, abandoned.

[51] Int. Cl.$^6$ ..................................................... C07C 5/25
[52] U.S. Cl. .......................... 585/363; 208/135; 502/306; 502/340; 502/341; 502/346; 502/430; 423/628
[58] Field of Search ....................... 502/306, 340, 502/341, 346, 430; 423/628; 585/363; 208/135

[56] References Cited

U.S. PATENT DOCUMENTS

| | | | |
|---|---|---|---|
| 2,740,820 | 4/1956 | Wilson et al. | 260/683.2 |
| 3,347,944 | 10/1967 | Fritz et al. | 260/666 |
| 3,405,196 | 10/1968 | Wolff | 260/683.2 |
| 3,577,473 | 5/1971 | Nagase et al. | 206/666 |
| 3,808,152 | 4/1974 | Nagase et al. | 252/463 |
| 3,897,509 | 7/1975 | Nagase et al. | 260/680 |
| 3,928,485 | 12/1975 | Nagase et al. | 260/680 |
| 4,205,192 | 5/1980 | Harada | 585/363 |
| 4,229,610 | 10/1980 | Myers | 585/664 |
| 4,248,852 | 2/1981 | Wakabayashi et al. | 423/626 |
| 4,675,307 | 6/1987 | Taniguchi et al. | 502/306 |
| 4,720,601 | 1/1988 | Suzukamo et al. | 585/377 |
| 4,727,204 | 2/1988 | Suzukamo et al. | 585/377 |
| 5,292,985 | 3/1994 | Lattner et al. | 585/671 |

*Primary Examiner*—Walter D. Griffin
*Assistant Examiner*—Nadine Preisch
*Attorney, Agent, or Firm*—Bradley A. Keller

[57] ABSTRACT

A process and catalyst for isomerizing olefins are disclosed. The process and catalyst are particularly useful for isomerizing alkenyl bridged ring compounds to the corresponding alkyladiene bridged ring compounds. In one embodiment, the isomerization catalyst comprises an oxygen treated mixture of an alkali metal on a dried support having a surface area of 125 to 195 m$^2$/g when the support consists essentially of alumina wherein the alumina precursor is a large crystallite pseudoboehmite. The catalyst is particularly useful for isomerizing 5-vinyl-2-norbornene to 5-ethylidiene-2-norbornene. The catalyst is very active and highly selective and resistant to catalyst poisons. The process contacts the catalyst with an alkenyl bridged ring compound and yields the corresponding alkyladiene bridged ring compound.

26 Claims, No Drawings

5,849,966

CATALYST AND PROCESS FOR THE ISOMERIZATION OF OLEFINS IN THE PRESENCE OF REACTIVE IMPURITIES

This application is a continuation-in-part of application Ser. No. 08/405,650, filed on Mar. 17, 1995, now abandoned, which is a continuation-in-part of application Ser. No. 08/150,946, filed on Nov. 12, 1993, now abandoned, which is a continuation-in-part of application Ser. No. 07/775,776, filed on Oct. 11, 1991, now abandoned, which is a continuation-in-part of application Ser. No. 07/700,016, filed on May 14, 1991, now abandoned, all of which are incorporated by reference in their entirety herein for purposes of U.S. practice.

FIELD OF THE INVENTION

The present invention relates to a process for isomerizing olefins, and particularly for isomerizing alkenyl bridged ring compounds to the corresponding alkylidene bridged ring compound by use of a highly active and highly selective isomerization catalyst in the presence of reactive impurities. The process of the invention may be used to isomerize 5-vinyl-2-norbornene (hereinafter "VNB") to 5-ethylidene-2-norbornene (hereinafter "ENB"), which is used commercially in the production of elastomeric polymers and synthetic rubber. The process of the invention may also be used to isomerize a terminal olefin to an internal olefin which may be used as a reactant in the synthesis of chemicals or as an alkylation feedstock to yield octane enhancing gasoline additives. The highly active isomerization catalyst is prepared by adding an alkali metal to alumina and then activating the mixture by careful oxidation of the alkali metal.

DESCRIPTION OF THE PRIOR ART

The isomerization of olefins is well-known. Olefins are often isomerized to produce the type of olefin necessary for a chemical synthesis or for a process for making fuels or fuel additives. For instance, the use of ENB as a monomer in the production of rubbery polymers is well known. ENB may be produced by reacting 1,3-butadiene and cyclopentadiene in an addition reaction commonly known as a Diels-Alder reaction, yielding VNB which is then catalytically isomerized to ENB.

Known isomerization catalysts include liquid bases, such as mixtures of alkali metal hydroxides and aprotic organic solvents, mixtures of alkali metal amides and amines, and mixtures of organic alkali metal compounds and aliphatic amines. Unfortunately, the catalytic activity of the liquid bases is relatively low, and therefore a large amount of these expensive catalysts must be used. Also, recovery of the catalyst from the reaction mixture is very difficult, requires complicated separation and recovery steps and consumes a large amount of energy.

Solid isomerization catalysts are also known, for example, alkali metals carried on large surface area anhydrous supports such as activated carbon, silica gel, alumina and the like. These solid catalysts are difficult to handle because they may ignite and lose activity on contact with oxygen. Also, the isomerization performance of these solid catalysts is poor, because conversion and selectivity are low.

U.S. Pat. No. 3,405,196 (Wolff) teaches the use of an alkali metal catalyst which is primarily used to convert 1-pentene to 2-pentene and 1-butene to 2-butene and is not used to isomerize alkenyl bridged ring compounds. The patent focuses on a process in which a terminal olefin is converted to an internal olefin in the presence of a supported alkali-metal catalyst that has been pretreated with an oxygen containing gas such as nitrous oxide. The catalyst used contains an alkali metal dispersed on a high-surface area, substantially inert support. The alkali metal may be selected from sodium, potassium, rubidium and cesium. The desired catalyst support material is a high surface area, large pore, and slightly acidic alumina.

The patent discloses a preferred temperature between 300° C. and 400° C. for dispersion of sodium on alumina. This would be impractical for commercial use since most catalyst preparation equipment can not function at such high temperatures.

The patent does not disclose the importance of surface area of the support and its relationship to resulting catalyst activity. The patent fails to teach or recognize the presence of any impurities in the olefin feed and does not disclose the importance of catalyst poisons or reactive impurities in the feed stream and its relationship to resulting catalyst activity.

Reactive impurities are defined to be such impurities in the feed stream which do not act as isomerization catalyst poisons, but are highly reactive and detrimental to use in the downstream process of polymerization.

U.S. Pat. No. 4,727,204 (Sumitimo) teaches a 5-vinyl-2-norbornene (VNB) feedstream can handle only up to 0.5 wt. % VCH impurity to make high purity ENB. When the VNB feedstream contains more than 0.5 wt % VCH, the quality of produced 5-ethylidene-2-norbornene (ENB) is unsatisfactory so that it cannot be used without additional purification as the third monomer in the production of EPDM. To produce ENB with high quality, it is essential to isomerize VNB containing less than 0.5 wt. % VCH.

The prior art catalysts are either pyrophoric or lack desirably high activities. These and other disadvantages of the prior art are overcome by the present invention, which provides a new selective and efficient catalyst for isomerization of olefins which, in addition, is resistant to catalyst poisons. Also the prior art is either silent on the issue of catalyst poisons or teaches that reactive feedstream impurities would inhibit the production of high purity ENB.

SUMMARY OF THE INVENTION

The present invention relates to a process and catalyst for isomerizing olefins, and particularly to isomerizing alkenyl bridged ring compounds to the corresponding alkylidene bridged ring compounds by use of a highly active and highly selective isomerization catalyst in the presence of reactive impurities contained in the olefins. In a preferred embodiment, the process of the invention is used for isomerizing an impure stream of 5-vinyl-2-norbornene (VNB) an alkenyl bridged ring compound, to make high purity quality 5-ethylidene-2-norbornene (ENB), an alkylidene bridged ring compound, which is used commercially as the diene monomer in ethylene-propylene-diene monomer rubber (EPDM).

One embodiment of the invention provides an activated isomerization catalyst prepared by:
  a) providing a substantially dry support material;
  b) mixing a metallic form alkali metal and the dry support material under conditions of time and elevated temperature to produce a catalyst precursor mixture comprising a substantially uniform dispersion of the alkali metal on the support;
  c) subjecting the catalyst precursor mixture to continued heat treatment at a temperature of at least 130° C. for a time of at least 30 minutes; and d) activating the heat treated catalyst precursor mixture by treatment with an oxygen-containing gas.

The invention also includes an isomerization process utilizing this activated catalyst for olefins. One preferred embodiment includes a process for catalytically isomerizing a stream comprising an alkenyl bridged ring compound which further comprises one or more reactive impurities which comprises contacting the stream comprising an alkenyl bridged ring compound which further comprises one or more reactive impurities with an activated catalyst, wherein the activated catalyst is prepared by:

a) providing a substantially dry support material wherein said substantially dry support material consists essentially of an alumina having a surface area in the range of 140 to 180 m$^2$/g when prepared from a starting material consisting of a large crystallite pseudoboehmite or having a surface area in the range of 230 to 260 m$^2$/g when prepared from a starting material consisting of a small crystallite pseudoboehmite;

b) mixing a metallic form alkali metal wherein said alkali metal is sodium and the dry support material under conditions of time and elevated temperature to produce a catalyst precursor mixture comprising a substantially uniform dispersion of the alkali metal on the support;

c) subjecting the catalyst precursor mixture to continued heat treatment at a temperature of at least 130° C. for a time of at least 60 minutes; and d) activating the heat treated catalyst precursor mixture by treatment with an oxygen-containing gas at a temperature of 150° C. to 200° C.

In yet another preferred embodiment, the invention provides for a process for catalytically isomerizing a stream comprising a 5-vinyl-2-norbornene which further comprises one or more reactive impurities which comprises contacting the stream comprising a 5-vinyl-2-norbornene which further comprises one or more reactive impurities with an activated catalyst, wherein the activated catalyst is prepared by:

a) providing a substantially dry support material wherein said substantially dry support material consists essentially of an alumina having a surface area in the range of 140 to 180 m$^2$/g when prepared from a starting material consisting of a large crystallite pseudoboehmite or having a surface area in the range of 230 to 260 m$^2$/g when prepared from a starting material consisting of a small crystallite pseudoboehmite;

b) mixing a metallic form alkali metal wherein said alkali metal is sodium and the dry support material under conditions of time and elevated temperature to produce a catalyst precursor mixture comprising a substantially uniform dispersion of the alkali metal on the support;

c) subjecting the catalyst precursor mixture to continued heat treatment at a temperature of at least 130° C. for a time of at least 60 minutes; and d) activating the heat treated catalyst precursor mixture by treatment with an oxygen-containing gas at a temperature of 150° C. to 200° C.

A feature of this invention is the high level of VNB conversion and the high selectivity to ENB in the presence of reactive impurities. Another feature of this invention is the stability of the catalyst used to effect isomerization. An object of the invention is to provide an isomerization catalyst which combines high selectivity and conversion efficiency and yet remains non-pyrophoric on contact with air or water. Accordingly, these and other features of this invention will become apparent from the following detailed description, wherein reference is made to the Figures in the accompanying drawings.

DETAILED DESCRIPTION OF THE INVENTION

Catalyst Preparation

The isomerization catalyst of the invention is comprised of an alkali metal on a dried support material. The preferred embodiment includes further treating the combination with a gas containing oxygen. The alkali metal may be selected from the group of lithium, sodium, potassium, rubidium, cesium and mixtures thereof. The alkali metal consists essentially of the metal in its elemental state, for example, if potassium is the alkali metal, it should be added as pure potassium and not in combination with another element, i.e., potassium hydroxide. Two or more alkali metals may be combined in the same catalyst. Sodium is the preferred alkali metal. The catalyst may be prepared by dispersing 1–40 wt % alkali metal on a dried support material at temperatures above the melting point of the alkali metal, under an atmosphere of dry, inert gas. The preferred embodiment includes the additional step of subjecting the alkali metal dispersed on the support material to oxidation by contact with a gas having an oxygen content of 0.1 to 25 mole % at temperatures of 0°–300° C. to both activate and passivate the catalyst.

Support—Composition

Oxides and/or hydroxides of metals of Groups 1A, 2A, 3A, 4A and 4B of the Periodic Table may be used as the support material but the support material may not be a hydrotalcite compound as described in U.S. Pat. No. 4,675,307. The Periodic Table referred to is the table as reproduced in the CRC Handbook of Chemistry and Physics, 53rd edition. Other examples of support materials include carbon, graphite, clays, diatomaceous earths, magnesia, titania, zirconia, calcium oxide, magnesium oxide, sodium oxide and barium oxide. The support may include one or more of these support materials. Alumina is the preferred support material and in a most preferred embodiment, the support material consists essentially of alumina. Alumina consists of mostly $Al_2O_3$ and small amounts of $Na_2O$, $SiO_2$ $TiO_2$, and $Fe_2O_3$. The alumina utilized in the most preferred embodiments is prepared from a small or large crystalline pseudoboehmite alumina. Gibbsite and Bayerite are not suitable starting aluminas.

Support—Pore Size

The pore size radius of the support material may range from about 5 to 1,000 Angstroms more preferably from 10 to 300 Angstroms and most preferably from 10 to 100 Angstroms. The support material used for preparing the catalyst may be in powder, pelletized, or extruded form. The support material should be dried under a dry atmosphere, and it should be free of water and entrained oxygen after calcination.

Support—Drying

In the preferred embodiment, the support should be dried of absorbed water prior to contact with the alkali metal. Drying is effected by heating the support material at temperatures of from 100° C. to 1,000° C., more preferably from about 200° C. to about 800° C. and most preferably from about 200° C. to about 400° C. The drying may be conducted at atmospheric pressure or higher, however, reduced pressures are preferred. Preferably an inert gas is purged through the drying vessel in order to sweep away any water or oxygen molecules which may be driven off from the support material by the heat. The drying should last for from about 0.1 to 100 hours preferably from about 1 to 20 hours. In the drying process, the support is heated at a constant temperature which drives water from the support material whereby no free water is left, thus producing an essentially dry support material. After drying, the support material should be kept under a dry atmosphere so that water does not become associated with the support material.

As mentioned above, drying at temperatures below 400° C. for less than 20 hours does not significantly change the surface area of alumina. However, drying at temperatures above 500° C. may result in a decrease in the alumina surface area.

Support—Surface Area

In fact, high temperature heating is used to reduce the surface area of starting aluminas from values above 195 $m^2/g$ or above 280 $m^2/g$ to values within the desired ranges of 125–195 $m^2/g$ and 220–280 $m^2/g$, respectively. For example, a large crystallite pseudoboehmite alumina with a surface area of 240 $m^2/g$ may be dried at 600° C. for 1 to 6 hours to yield an alumina with a surface area of 170 $m^2/g$.

The material of the support upon which the alkali metal should be dispersed may be any normally solid material which has large pores. In the most preferred embodiment, the material is alumina and is not a hydrotalcite compound as described in U.S. Pat. No. 4,675,307. The support material should remain in the solid state at the elevated temperatures required during drying and alkali metal dispersion.

The preferred surface area range for alumina is a function of the starting material. The preferred starting material for the alumina support is pseudoboehmite, which may be further differentiated by their crystalline sizes, being large or small. Alumina supports prepared by heating of gibbsite or Bayerite aluminas can not be used in the present invention. Calcination is used to reduce the surface area of these materials by methods well known in the art in order to obtain the desired surface area.

The preferred surface area ranges from 125 to 195 $m^2/g$ after heating, when prepared from a large crystalline pseudoboehmite such as a catapal grade alumina. Preferably, the support material has a surface area ranging from about 130 to 190 $m^2/g$, more preferably from about 140 to 180 $m^2/g$, and most preferably from about 150 to 180 $m^2/g$. In fact, some surprisingly active catalysts have been prepared from support material with a surface area of about 170 $m^2/g$. Catalysts with a surface area of about 180 $m^2/g$ are also good.

The preferred surface area ranges from 220 to 280 $m^2/g$ after heating, when prepared from a small crystalline pseudoboehmite. Preferably, the support material has a surface area ranging from about 230 to 270 $m^2/g$, and more preferably from about 230 to 260 $m^2/g$.

Heating, as described herein, at temperatures below 400° C. does not significantly change the surface area of the support. The surface area of the alumina is measured by the BET (Brunauer, Emmett, Teller) method of nitrogen adsorption and desorption.

Application of Metal Into Support material

The catalytic combination of alkali metal and support material is prepared by first contacting the dried support material with the alkali metal under a dry, inert, oxygen free atmosphere thus forming a catalyst precursor mixture. The alkali metal is preferably in the molten state during at least a portion of the contact and the contact occurs by physically blending the dried support material with the alkali metal under the dry, inert, oxygen free atmosphere. In the most preferred embodiment, the catalyst precursor mixture consists essentially of the alkali metal and the support material.

The alkali metal may be in the solid, liquid or gaseous state when initially contacted with the dried support material. Usually, the initial contact occurs at a temperature above the melting point of the metal, preferably from about 1000° to about 150° C. under an inert atmosphere. Gasses such as nitrogen, argon, helium and krypton will provide an inert atmosphere. If the alkali metal is in the solid state when initially contacted with the support material, the temperature of the mixture should be raised enough to melt the alkali metal, and the mixture should be stirred for initial dispersion of the alkali metal on the support material. A preferred method for mixing sodium with alumina is to add molten sodium to a gas fluidized bed of alumina powder at a temperature above the melting point of Na.

The mixing agitation may be discontinued after the alkali metal is roughly dispersed on the support material, however, it is preferable to continue mixing until the alkali metal is evenly distributed on the surface of the dried support material. In the case of a mixture of sodium on alumina, a visual indication of a blue black or blue gray evenly distributed color over the surface of the alumina indicates uniform distribution of sodium. If large amounts of materials are to be mixed or slow mixing speeds are used, complete uniform dispersion will take longer, however, mixing is often complete within about 30 minutes when a rotary mixer is used to produce 100 grams of catalyst.

The amount of alkali metal which should be distributed upon the dried support material is in the range of from about 1 to about 40 wt % based upon the total weight of the mixture comprising both alkali metal and dried support material. Preferably the range of alkali metal is from about 5 to about 20 wt % and most preferably from about 10 to about 15 wt %.

Heat Treat

In a preferred embodiment, after dispersion of metal on the support, the uniform dispersion should be agitated for 1–10 hours, preferably 2 hours, at the same temperature or higher to ensure complete thermal mixing. The amount of time required for the heat soak step is a function of mixing temperature. The higher the temperature, the shorter the heat treat time. The temperature should be in the range of the melting point of the alkyaline metal to 400° C. preferably in the range of 130° C. to 300° C. most preferably in the range of 150° C. to 250° C.

At a mixing temperature of 150° C., 2 hours is most preferred and is equivalent to 200° C. for 1 hour treatment.

Oxidation

After the alkali metal has been dispersed upon the dried support material and heat soaked to form a catalyst precursor mixture, the mixture should be contacted with an activating gas containing oxygen. Since a violent reaction between the alkali metal and oxygen will occur if oxygen is added too quickly, care should be taken to avoid exposing the mixture to excessive oxygen initially. If the temperature of the mixture exceeds about 300° C. during the activation, the rate of oxygen contact with the mixture should be reduced. The rate of oxygen contact may be reduced by lowering the flow rate of oxygen containing gas or by reducing the concentration of oxygen in the oxygen containing gas. Some inert gas flow should be maintained in order to reduce the temperature of the catalyst mixture to a safe level. Alternatively, pure oxygen at reduced pressure may be used as the activating gas.

In one embodiment of the invention, the catalyst mixture is contacted with the activating gas at a temperature within the range of from about 0° to about 300° C. preferably about 1000° to 250° C. and most preferably about 150° to about 200° C. The catalyst mixture may be agitated while the contact with the activating gas occurs.

The activating gas may comprise a single type of gaseous compound containing oxygen or a mixture of an inert gas with another gas containing oxygen. The activating gas must be dry, since moisture will hinder the ultimate catalyst performance. Examples of activating gases include nitric oxide, nitrous oxide, sulfur dioxide, dry air, ozone, and mixtures of oxygen with nitrogen, helium, argon, krypton, xenon, or radon. Mixtures of these gases or mixtures may also be used. In a preferred embodiment a mixture of oxygen ($O_2$) in nitrogen ($N_2$) may be used as the activating gas. The amount of oxygen in the activating gas should be from about 0.1 to about 25 mole %. Preferably the amount of oxygen in the activating gas mixture is from about 2 to about 10 mole % and most preferably about 5 mole %. If pure oxygen (100 mole % $O_2$) is used as the activating gas, the pressure should be reduced to between about 0.001 and 0.25 atmosphere.

If oxygen is only part of an oxygen containing molecule, such as NO or $NO_2$, the oxygen content of the gas is calculated by dividing the atomic weight of oxygen in the molecule by the molecular weight of the gas.

The contact between the oxygen containing gas and the mixture may be continued until all of the alkali metal has been oxidized; however, it is preferable to stop the contact when the total contact oxygen to alkali metal atomic ratio is within the range of from about 0.005 to about 1.0 moles of oxygen per atom of alkali metal. Preferably the ratio is within the range of from about 0.01 to 0.2, more preferably 0.05 to 0.18 and most preferably 0.1 to 0.18 moles of oxygen per atom of alkali metal. These ranges reflect the total moles of oxygen contacted with the alkali metal. At these ranges most, usually all, of the oxygen contacted with the alkali metal reacts with the alkali metal. This is apparent in FIG. 2 where contact of more than 0.5 moles of oxygen per atom of sodium does not result in further change in catalyst activity.

Isomerization

The catalyst prepared as described above is then used to isomerize olefins.

The isomerization of olefins described herein relates to the movement of the olefinic double bond from its initial position in the olefinic molecule. It is often necessary to change the location of the double bond in order to provide the proper reactant for a desired chemical synthesis. For instance, linear alpha olefins such as 1-butene, 1-pentene, 1-hexene, 1-heptene, and 1-octane may be isomerized to yield internal olefins such as 2-butene, 2-pentene, 2-hexene, 3-hexene, 2-heptene, 3-heptene, 2-octene, 3-octene and 4-octene. Additionally, branched alpha olefins such as 2-methyl-1-butene and 3-methyl-1-pentene may be isomerized to 2-methyl-2-butene and 3-methyl-2-pentene, respectively. Internal olefins and branched internal olefins may also be isomerized according to the invention which may be used to isomerize any olefin with three or more carbon atoms.

The invention is particularly useful in the production of ENB from VNB. The VNB stream to be isomerized may be 90% or more by volume VNB or the VNB stream may be diluted with a solvent that is inert during the isomerization process. Appropriate solvents include aliphatic compounds such as hexane, heptane, octane and isooctane, and aromatic compounds such as benzene, toluene, xylene and ethylbenzene.

The catalyst may be used to isomerize alkenyl bridged ring compounds, such as VNB, to alkylidene bridged ring compounds, such as ENB. Alkenyl bridged ring compounds are of the general formula (I):

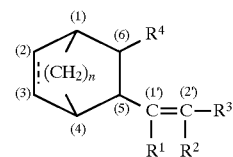

wherein $R^1, R^2$ and $R^3$ are each hydrogen or alkyl having 1 to 8 carbon atoms, $R^4$ is hydrogen or alkyl having 1 to 4 carbon atoms, and n is 1 or 2 and wherein a double bond may be present at the place between the 2- and 3-positions as indicated by the dotted line.

Specific examples of some alkenyl bridged ring compounds are:

5-vinylbicyclo[2,2,1]heptane;
5-(1'-propenyl)-bicyclo[2,2,1]heptane;
5-(1'-butenyl)-bicyclo[2,2,1]heptane;
5-isopropenylbicyclo[2,2,1]heptane;
5-(2'-methyl-1'-propenyl)bicyclo[2,2,1]heptane;
6-methyl-5-vinylbicyclo[2,2,1]heptane;
6-methyl-5-isopropenyl[bicyclo[2,2,1]heptane;
6-ethyl-5-vinylbicyclo[2,2,1]heptane;
5-vinylbicyclo[2,2,1]hepta-2-ene;
5-(1'-propenyl)-bicyclo[2,2,1]hepta-2-ene;
5-(1'-butenyl)-bicyclo[2,2,1]hepta-2-ene;
5-isopropenylbicyclo[2,2,1]hepta-2-ene;
5-(2'-methyl-1-propenyl)-bicyclo[2,2,1]hepta-2-ene;
5-(1'-octenyl)-bicyclo[2,2,1]hepta-2-ene;
6-methyl-5-vinylbicyclo[2,2,1]hepta-2-ene;
6-methyl-5-isopropenylbicyclo[2,2,1]hepta-2-ene;
6-ethyl-5-vinylbicyclo[2,2,1]hepta-2-ene;
5-vinylbicyclo[2,2,1]octane;
5-(1'-propenyl)-bicyclo[2,2,2]octane;
5-isopropenylbicyclo[2,2,2]octane;
5-(1'-butenyl)-bicyclo[2,2,2]octane;
6-methyl-5-vinylbicyclo[2,2,2]octane;
6-methyl-5-isopropenylbicyclo[2,2,2]octane;
5-vinylbicyclo[2,2,2]octane;
5-(1'-propenyl)-bicyclo[2,2,2]octa-2-ene;
5-isopropenylbicyclo[2,2,2]octa-2-ene;
5-(1'-butenyl)-bicyclo[2,2,2]octa-2-ene;
5-(2'-methyl-1'-propenyl)-bicyclo[2,2,2]octa-2-ene;
6-methyl-5-vinylbicyclo[2,2,2]octa-2-ene; and
6-methyl-5-isopropenylbicyclo[2,2,2]octa-2-ene.

The compounds represented by formula I can be produced by subjecting a cyclic diene such as cyclopentadiene or cyclohexadiene and an aliphatic 1,3-diene to a Diels-Alder reaction or by subjecting the corresponding bridged ring compound bearing a hydroxyl group at the 1'- or 2'- position to dehydration.

Isomerization of an alkenyl bridged ring compound shifts the double bond from 1'-2' position to the 5-1' position of formula I thereby forming the alkylidene bridged ring compound. The isomerization is effected by contacting an alkenyl bridged ring compound, for example, a VNB stream, with the catalyst at temperatures of from about −50° C. to about 200° C. Preferred temperatures of isomerization range from about 0° to about 150° C., most preferably from about 20° C. to about 100° C.; however, to achieve high equilibrium conversion, the final reaction temperature should be less than 30° C.

Although alkenyl bridges ring compounds can be obtained essentially pure by distillation, it is convenient economically to purify these compounds to a lessor degree. However, many of the remaining impurities are reactive to strong base catalysts and can act as a catalyst poison. Surprisingly, the sodium on alumina catalysts show good poisoning resistance at low isomerization temperatures.

Such reactive impurities include mono olefins, acidic oxygenates, and diene impurities, which include the following:

cyclopentadiene (CPD)
cyclooctadiene (COD)
tetrahydroindene (THI)
vinylnorbornadiene (VNBD)
ethynylnorborene (EYNB)
hydroperoxides
vinylcyclohexenes (VCH)
methyl vinylcyclohexenes (MVCH)

The prior art teaches only that CPD has a poisoning effect on the catalyst which results in the loss of catalyst. The other diene impurities are not mentioned in the prior art of isomerization of alkenyl bridged ring compounds. Moreover, these impurities will have deleterious effect on ENB used to make EPDM rubber. In contrast, the catalyst of the invention can perform in the presence of all of these impurities to give ENB which is acceptable for use in downstream polymerization manufacturing processes.

CPD is strongly adsorbed onto the isomerization catalyst and is therefore removed and not included in the isomerization product to give a higher purity product. The CPD levels in the olefin feed stream may be from 1–1000 wppm of the impurity, preferably from 5 to 500 wppm, and most preferably from 10–50 wppm.

COD is isomerized by the isomerization catalyst to the 1,3 isomer which is unreactive and not detrimental to use in the downstream polymerization process. This effectively gives a higher quality isomerization product. The catalyst can perform in the presence of from 1–10,000 wppm of the COD impurity, preferably from 5 to 1000 wppm, and most preferably from 10–500 wppm.

THI dehydrogenates with the isomerization catalyst to indan and indene. The indan is isomerized to a non-reactive impurity and the indene is adsorbed and thereby removed from the product stream to give a higher purity product. The catalyst of the invention can perform in the presence of from 1–5000 wppm of THI impurity, preferably from 5 to 1000 wppm, and most preferably from 10 to 100 wppm.

Both VNBD and EYNB are adsorbed into the isomerization catalyst and thereby removed by from the isomerization product stream to give a higher purity product. The catalyst can perform in the presence of from 1–2000 wppm of each of the VNBD and EYNB impurities, preferably from 5 to 1000 wppm, and most preferably from 10 to 500 wppm.

The hydroperoxides are adsorbed by the catalyst and therefore, are removed and are not present in the product stream to give a higher purity product. The catalyst of the invention can perform in the presence of from 1–500 wppm of this impurity, preferably from 5 to 100 wppm, and most preferably from 10–50 wppm.

VCH and MCVH dehydrogenate to give aromatic compounds which are unreactive and not detrimental to use in down-stream polymerization process. This effectively gives a higher quality isomerization product.

The catalyst can also perform in the presence of quantities of up to 90 wt. % being vinylcyclohexene (VCH) and/or methyl vinylcyclohexene (MVCH), preferably from 0.5 to 90 wt % VCH, more preferably from 0.5 to 50 wt. % VCH, and most preferably from 0.5 to 30 wt. % VCH. The levels of these two typical impurities have been found to not effect the catalyst performance.

The amount of catalyst used is primarily determined by poison levels, although the use of more catalyst will reduce the time necessary to bring about a given level of conversion at the same temperature. Generally, the weight of alkali metal utilized per weight of alkenyl bridged ring compound ranges from 1 part alkali metal per 10,000 parts of alkenyl bridged ring compound to 1 part alkali metal per 500 parts of alkenyl bridged ring compound. In fixed bed processes, the weight average space velocity expressed in terms of weight of feed per hour divided by the weight of the supported catalyst in the fixed bed should range between 0.1 to 500 $Hr^{-1}$.

The isomerization process may be conducted at any pressure, however, pressures of from about 0 to about 100 psig are preferred. The reaction may be conducted in liquid phase or gas phase. A preferred method for conducting the isomerization is to mix a powdered catalyst in a stream of liquid olefin wherein the solid catalyst is suspended in the liquid, such as by stirring. Such a method is disclosed in U.S. Pat. No. 5,292,985 entitled "Method of Preparing Isomerization Catalyst", which is hereby incorporated by reference. Reaction time varies depending on the reaction temperature, and the amount of catalyst used, but generally ranges from 5 minutes to 6 hours. The isomerization reaction is generally conducted in the absence of oxygen and water.

Use of the above described catalyst of the invention in the isomerization of VNB to ENB usually results in nearly complete conversion to ENB and therefore no product purification is necessary. The resulting ENB may be transferred directly to a polymerization process to make EPDM rubber. If for some reason the conversion rates are lower, the ENB may be purified of VNB by distillation.

Although the isomerization of VNB to ENB has been described in more detail, the catalyst is also useful in the isomerization of olefins in general in the same way as described in reference to VNB isomerization. Conversion percentages herein are determined by subtracting the weight amount of compound remaining after isomerization from the beginning amount of the compound and dividing the result by the beginning amount of the compound. The resulting quotient is multiplied by 100% to express the term in percent. Selectivity is determined by dividing the amount of material converted into desired product by the total amount of material converted and multiplying the result by 100% to express the term in percent.

Particular aspects of the invention may be further understood by reference to the examples below. While these examples are provided to fully illustrate and describe specific features of the invention, they should not be construed as limitations on the scope of the invention, which is fully described above.

EXAMPLE I

Invention and Comparatives

Alumina powder (30 g) previously dried for 1 hour at 400° C. was placed in a round bottom flask under a nitrogen blanket at room temperature along with 4.5 g sodium metal which had been cut into small pieces. The mixture inside the round bottom flask was stirred and heated to 150° C. for 60 minutes. The sodium metal dispersed onto the alumina resulting in a blue-gray powder.

That mixture was then heated to a temperature of 410° C. and stirring was continued for 60 minutes for heat treat step under a nitrogen atmosphere. Thus the mixing and the heat treat steps were conducted at two different temperatures. The sodium/alumina mixture was cooled to room temperature after which, a gaseous stream of 5% $O_2$ in $N_2$ was passed through the flask at a rate of 126 ml/min until the molar ratio of $O_2$ to the initial amount of Na was 0.2:1.

Pure VNB was contacted with 1 or 2 wt % of the catalyst prepared as noted above. The VNB/catalyst solution was stirred at room temperature for 1 hour. A sample of the resulting solution was taken and the conversion of VNB was measured. The activity rate constant was calculated according to the following formula: $[\ln(VNB^i/VNB^f)] \div [(\text{catalyst wt \% Na})(\text{reaction time in hours})]$, where $VNB^i$ is the initial concentration of VNB, and $VNB^f$ is the concentration of VNB at the designated reaction time. The figure clearly shows that when alumina support material is prepared by heating a large crystallite pseudoboehmite to give a surface area within the range of 125–195 $m^2/g$, the activity of the catalyst for this reaction can be significantly improved over activities of catalysts outside of the desired surface area range. More preferably, the surface area of the alumina should be between 130 and 190 $m^2/g$, 140 to 180 $m^2/g$ and most preferably 150 to 180 $m^2/g$. The most active catalyst is prepared from alumina with a surface area of about 170 $m^2/g$.

TABLE 1

| Exp No. | Alumina Precursor Material | Example Type | Surface Area | Catalyst Activity |
|---|---|---|---|---|
| 1 | Large Crystallite Pseudoboehmite | Comparative | 6 | 1 |
| 2 | Gibbsite | Comparative | 85 | 47 |
| 3 | Gibbsite | Comparative | 100 | 29 |
| 4 | Gibbsite | Comparative | 115 | 23 |
| 5 | Gibbsite | Comparative | 126 | 9 |
| 6 | Gibbsite | Comparative | 127 | 14 |
| 7 | Gibbsite | Comparative | 136 | 52 |
| 8 | Large Crystallite Pseudoboehmite | Invention | 141 | 46 |
| 9 | Large Crystallite Pseudoboehmite | Invention | 163 | 150 |
| 10 | Large Crystallite Pseudoboehmite | Invention | 156 | 165 |
| 11 | Large Crystallite Pseudoboehmite | Invention | 167 | 199 |
| 12 | Large Crystallite Pseudoboehmite | Invention | 172 | 158 |
| 13 | Large Crystallite Pseudoboehmite | Invention | 178 | 87 |
| 14 | Large Crystallite Pseudoboehmite | Comparative | 201 | 31 |
| 15 | Gibbsite | Comparative | 220 | 14 |
| 16 | Large Crystallite Pseudoboehmite | Comparative | 230 | 25 |
| 17 | Large Crystallite Pseudoboehmite | Comparative | 130 | 37 |
| 18 | Large Crystallite Pseudoboehmite | Invention | 141 | 46 |
| 19 | Large Crystallite Pseudoboehmite | Invention | 164 | 262 |

EXAMPLE II

Comparative

This example shows the preparation of a catalyst prepared from an alumina with a surface area outside of the preferred range and with a lower heat treat temperature. Alumina powder (30 g) prepared by heating a large crystallite pseudoboehmite to give a surface area of 200 $m^2/g$ and 4.5 g sodium metal, cut into pieces, or placed into a round bottom flask under a nitrogen atmosphere at room temperature. The mixture was stirred and heated to 150° C. for 30 minutes. During this step, the sodium metal was dispersed onto the alumina resulting in a bluish-gray powder. The stirring was continued while the temperature was maintained at 150° C. for 60 minutes. The mixture was then cooled to room temperature. A gaseous stream of nitrogen containing 5 mole % oxygen was passed through the round bottom flask at a rate of 126 ml/min until the molar ratio of $O_2$ to initial sodium was 0.2:1. The activity rate constant for this catalyst for isomerization of VNB to ENB at room temperature was measured as 15. The test was repeated except that the heat treat temperature was 300° C.

Comparison of these two results show that the temperature of mixing sodium and alumina leads to different catalytic activity even for catalysts with surface areas outside of the ranges preferred in the invention.

TABLE 2

| Example | Heat Treat Temperatures °C. | Catalyst Activity |
|---|---|---|
| First | 300 | 31 |
| Second | 150 | 15 |

EXAMPLE III

Invention and Comparative

This example shows the preferred amounts of $O_2$ added to a catalyst during catalyst preparation.

In each of four separate preparations of catalysts, 30 g alumina powder with a surface area of 178 $m^2/g$, prepared by heating a large crystallite pseudoboehmite and 4.5 g sodium metal, cut into pieces, were placed in a round bottom flask under a nitrogen atmosphere at room temperature. The mixture was stirred and heated to a temperature of 150° C. for 30 minutes. After 30 minutes, the sodium metal was dispersed onto the alumina and the powder had changed in color to bluish-gray. The temperature of the mixture was then raised to 300° C. for 60 minutes while stirring continued. The mixture was then cooled to room temperature. A nitrogen stream containing 5 vol. % oxygen was then passed through the flask at 126 ml/min until the ratio of $O_2$ to initial sodium was 0.1:1. The catalyst preparation was repeated except that the nitrogen stream containing 5 vol. % $O_2$ was passed through the flask until the ratio of $O_2$ to initial sodium was 0.2:1. A third catalyst was prepared in a similar manner so that the ratio of $O_2$ to initial sodium was 0.5:1. A fourth catalyst was prepared in the same manner except that no oxygen was added to the mixture of sodium dispersed on alumina. The results of an analytical test to determine the amount of unreacted sodium on the catalyst is set forth below in Table 2.

TABLE 3

| Example | $O_2$/Na Ratio | Example Type | % Unreacted Na Metal | Catalyst Activity |
|---|---|---|---|---|
| First | 0.1/1 | Invention | 33 | 340 |
| Second | 0.2/1 | Comparative | 5 | 5 |
| Third | 0.5/1 | Comparative | 5 | 5 |
| Fourth | 0/1 | Comparative | 81 | 40 |

The isomerization activity of the four catalyst prepared above was measured.

As demonstrated in Examples I, II, and III, the catalyst prepared with alumina prepared from a large crystallite pseudoboehmite to have a surface area of about 180 $m^2/g$ performed better than those catalysts having aluminas with surface areas of either 155 or 210 $m^2/g$. Aluminas with surface areas of about 170 $m^2/g$ are most preferred.

EXAMPLE IV

These examples illustrate the effect of varying parameters of oxidation, heat treat temperatures and time and the isomerization of other olefins, in addition to VNB.

Example 4.1

A first catalyst, Catalyst A, was prepared by starting with 30 g alumina powder (particle size 20–200 micron), surface area of 178 $m^2/g$, prepared by heating a large crystallite pseudoboehmite, was dried at 400° C. for 1 hour. It was then placed in a round bottom flask under nitrogen at room temperature along with sodium metal pieces (4.5 g). The mixture was stirred and heated to 150° C. internal temperature for 30 min. During this step, the sodium metal dispersed onto the alumina to give a bluish or gray powder. The mixture was then heated in a soaking step to an internal temperature of 300° C., and stirred for 60 min. except the mixture was oxidized by passing 5% $O_2$ in $N_2$ through the flask at 126 ml/min with stirring until the ratio of $O_2$ to starting Na was 0.2:1. The amount of $O_2$ added was the stoichiometric amount needed to convert all the unreacted sodium to $Na_2O$. Temperature during the oxidation was 50°–70° C. Analysis of this catalyst showed that 5% of the starting sodium metal remained unreacted (due to the oxidation).

The catalyst was tested for isomerization activity of 5-vinyl-2-norbornene to 5-ethylidene-2-norbornene. The procedure was to add 5-vinyl-2-norbornene (25 g) to catalyst (0.25 g) with stirring at room temperature under $N_2$. After one hour, a sample was withdrawn and analyzed by gas chromatography. An activity number was calculated as [In $(C_O/C)$]×$10^2$, where $C_O$ and C are respectively the initial and final concentrations of 5-vinyl-2-norbornene.

The catalyst preparation method for Catalyst A was repeated except for varying the starting surface areas resulting in Examples B, C, D, E, F. The catalysts were then tested for unreacted Na and isomerization activity by the procedure given in Example 1. The results are tabulated below in Table 4.1.

TABLE 4.1

| Catalyst Example | Example Type | Alumina Surface Area | Na Unreacted % | Activity Number |
|---|---|---|---|---|
| A | Invention | 175 | 5 | 120 |
| B | Comparative | 200 | 6 | 30 |
| C | Invention | 167 | 19 | 250 |
| D | Invention | 140 | 25 | 50 |
| E | Invention | 126 | 52 | 40 |
| F | Comparative | 115 | —* | 20 |

*Not measured

The results shown in Table 4.1 demonstrate a preferred range of surface areas from 125 to 195 $m^2/g$ for the alumina support material that gives a catalyst with a higher isomerization activity than those with a surface area outside this range. A more preferred range is 140–180 $m^2/g$ and a most preferred range is 150–170 $m^2/g$.

Example 4.2

The catalysts were then tested for isomerization activity other than VNB to ENB.

Catalysts prepared in Examples B–E were tested for activity to isomerize 3-methyl-1-pentene, 2-methyl-1-butene, 4-methyl-1-pentene, and 1-pentene. The procedure was to add olefin (30 ml) to catalyst (0.25 g) under nitrogen at 0° C. with stirring. After one hour a liquid sample was removed and analyzed by gas chromatography. An activity number was calculated in Example 1 except $C_O$ and C are respectively the initial and final concentrations of olefin.

The results shown in Table 4.2 below again demonstrate that catalyst activity is greatest when the starting alumina when prepared by heating a large crystallite pseudoboehmite has a surface area below 200 $m^2/g$. Although there was some effect of olefin structure on isomerization activity, the most generally high activity catalyst was prepared from alumina which had a surface area in the most preferred range found for 5-vinyl-norbornene isomerization.

TABLE 4.2

| Catalyst Example | Example Type | Alumina Surface Area | Activity Number | | | |
|---|---|---|---|---|---|---|
| | | | 3-Methyl-1-Pentene | 2-Methyl-1-Butene | 4-Methyl-1-Pentene | 1-Pentene |
| B | Comparative | 200 | 1 | 1 | 1 | 1 |
| C | Invention | 167 | 520 | 160 | 55 | 80 |
| D | Invention | 140 | 120 | 240 | 15 | 200 |
| E | Invention | 126 | 70 | 50 | 12 | 180 |

Example 4.3

Three tests were run to quantify the effect of heat treat temperatures. Catalysts G, H, and I were prepared by the same procedure as Catalyst A, except with different soak temperatures. The activity of the catalysts prepared were tested for isomerization of VNB by the same procedure used in Example 4.1.

TABLE 4.3

| Catalyst Example | Example Type | Heat Treat Temperature (°C.) | Activity Number |
|---|---|---|---|
| G | Invention | 150 | 200 |
| H | Invention | 200 | 260 |
| I | Invention | 240 | 230 |
| A | Comparative | 300 | 120 |

The results shown in Table 4.3 demonstrate that catalyst activity is highest when the soak temperature is about 200° C.

Example 4.5

Tests were run to get a comparison on the oxidation level and soak temperature. Catalysts G, J, and K were prepared by the same method as Catalyst A, except with different soak temperatures and oxidation levels. The activity of the catalysts was tested.

TABLE 4.5

| Catalyst Example | Example Type | $O_2$/Na Ratio | Heat Treat Temperature | Na Unreacted % | Activity Number |
|---|---|---|---|---|---|
| K | Invention | 0.2/1 | 150° F. | 11 | 200 |
| L | Invention | 0.1/1 | 150° F. | 50 | 100 |
| A | Invention | 0.2/1 | 300° F. | 5 | 120 |
| c | Invention | 0.1/1 | 300° F. | 33 | 340 |

The results in Table 4.5 demonstrate that catalyst activity is highest when soak temperature is 300° F. and oxidation level of 0.1/1.

Example 4.6

A safer catalyst can be made when alumina (30 g) with a surface area of 167 $m^2/g$ was dried for one hour at 400° C.

and cooled under vacuum. This alumina was then mixed under $N_2$ with sodium metal pieces at 150° C. The mixture was oxidized with 5% $O_2$ in $N_2$ at 60°–80° C. until the ratio of $O_2$/Na was 0.1/1. This procedure was repeated except the time of the soak step was lengthened to 120 min.

The catalysts were then tested for isomerization activity, the results are tabulated below:

TABLE 4.6

| Catalyst Example | Example Type | Soak Time | Na Unreacted % | Activity Number |
|---|---|---|---|---|
| 6a | Invention | 60 min. | 50 | 30 |
| 6b | Invention | 120 min. | 50 | 410 |

These results show that by lengthening the time of the soak step at 150° C., a higher activity catalyst is obtained.

Example 4.7

It would be best from a catalyst manufacturing perspective, if the catalyst preparation could be carried out all at 150° C., including the oxidation step. The oxidation step of the catalyst preparation is exothermic by 430 Btu/Lb. and would probably be the most time consuming step in large scale preparations. To augment heat removal rate, it would be best to run oxidation at as high a temperature as possible. Given this 150° C. temperature constraint, two additional examples were run.

Alumina (30 g) with a surface area of 178 $m^2$/g prepared by heating a large crystallite pseudoboehmite was dried for one hour at 400° C. and cooled under vacuum. This alumina was then mixed under $N_2$ with sodium metal pieces at 150° C. for 30 min, and then mixed in a soak step at the same temperature for 120 min. The mixture was then oxidized with 5% $O_2$ in $N_2$ while maintaining internal temperature between 150° and 180° C. until the ratio of $O_2$/Na was 0.15/1. Analysis showed 10% of the starting sodium remained unreactive. This catalyst was tested for activity to isomerize 5-vinyl-2-norbornene with the procedure of Example 1.

This same catalyst preparation procedure was repeated, but with an alumina starting material that had a surface area of 167 $m^2$/g.

TABLE 4.7

| Catalyst Example | Example Type | Surface Area, $m^2$/g | Na Unreacted % | Activity Number |
|---|---|---|---|---|
| 7a | Invention | 178 | 10 | 520 |
| 7b | Invention | 162 | — | 550 |

An activity number of 550 is the highest activity number possible with this procedure, and represents the equilibrium conversion of 5-vinyl-2-norbornene to 5-ethylidene-2-norbornene.

EXAMPLE V

Effect of Reactive Impurities

These examples show the effect of reactive impurities in the isomerization of VNB to ENB, as well as the effect of starting material of the alumina. The catalysts are prepared using various conditions.

| Catalyst Example | Description Sub Title |
|---|---|
| A | Comparative — No oxidation — Stir — Metallic |
| B | Invention — Oxidation — Molten — Agitation |
| C | Invention — Oxidation — Stir Metallic |
| D | Comparative — Outside Range — No Oxygen |
| E | Comparative — Outside Range — Oxidation |
| F | Comparative — Outside Range — Oxidation |
| G | Invention — Inside Range — Starting Material |
| H | Comparative — Outside Range — Starting Material |
| I | Comparative — Outside Range — Starting Material |

EXAMPLE A

Comparative—No oxidation—Stir—Metallic

This example describes one method of catalyst preparation. First, alumina (30 g), prepared by heating a large crystallite pseudoboehmite to give a surface area of 167 $m^2$/g and a 1.2 wt % loss on ignition at 1150° C. is dried in a nitrogen flow at 400° C. for 1 hour and then cooled to room temperature under nitrogen. Then, small pieces of metallic sodium (4.5 g) and alumina are placed in a 300 ml round bottom flask equipped with a mechanically driven stir paddle. The mixture is heated under nitrogen to 150° C., and at the point metallic sodium starts to melt, stirring is started. The mixture is stirred for 2.5 hours, and then cooled to room temperature.

EXAMPLE B

Invention—Oxidation—Molten—Agitation

This example describes another method of catalyst preparation. First, alumina (80 lbs), prepared by heating a large crystallite pseudoboehmite to give a surface area of 172 $m^2$/g and a 1.2 wt % loss on ignition at 11 50° C. is dried at 350° C. for 1 hour in a nitrogen flow. The alumina is cooled to 150° C., and molten sodium (12 lb) is added at 6 lb/hr under nitrogen with agitation. The mixture is stirred 2 hours, and then a mixture of 5% $O_2$ in $N_2$ is added at 90 L/min while maintaining the temperature between 150°–200° C. The final $O_2$/Na ratio is 0.18/1.

EXAMPLE C

Invention—Oxidation—Stir Metallic

This example describes another method of catalyst preparation. First, alumina (30 g), prepared by heating a large crystallite pseudoboehmite to give a surface area of 167 $m^2$/g and a 1.2 wt % loss on ignition at 1150° C. is dried in a nitrogen flow at 400° C. for 1 hour and then cooled to room temperature under nitrogen. Then, small pieces of metallic sodium (4.5 g) and alumina are placed in a 300 ml round bottomed flask equipped with a mechanically driven stir paddle. The mixture is heated under nitrogen to 150° C., and at the point metallic sodium starts to melt, stirring is started. The mixture is stirred for 2.5 hours, and then cooled to room temperature. Then, 5% $O_2$ in $N_2$ is added at 126 ml/min until the ratio of $O_2$/Na is 0.15/1.

EXAMPLE D

Comparative—Outside Range—No Oxygen

This example describes another method of catalyst preparation. First, alumina (20.5 g), a large crystallite pseudoboehmite with a surface area of 250 m²/g and a 2.7 wt % loss on ignition at 150° C., is dried in a nitrogen flow at 400° C. for 1 hour, and cooled to room temperature under nitrogen. Then pieces of metallic sodium (1.7 g) and alumina are placed in a 300 ml round bottomed flask equipped with a mechanically driven stir paddle. The mixture is heated under nitrogen to 150° C., and at the point metallic sodium starts to melt, stirring is started. The mixture is stirred for 2.5 hours and then cooled to room temperature.

EXAMPLE E

Comparative—Outside Range—Oxidation

This example describes a method of catalyst preparation where alumina (17 g), prepared by heating large crystallite pseudoboehmite to give a surface area of 200 m²/g is dried in a nitrogen flow at 400° C. for 1 hour and then cooled to room temperature under nitrogen. Then, small pieces of metallic sodium (2.5 g) and alumina are placed in a 300 ml round bottomed flask equipped with a mechanically driven stir paddle. The mixture is heated under nitrogen to 150° C., and at the point metallic sodium starts to melt, stirring is started. The mixture is stirred for 30 min., and then heated to 300° C. for one hour. The mixture is then cooled to room temperature, and 5% $O_2$ in $N_2$ is added at 126 ml/min until the ratio of $O_2$/Na is 0.2/1.

EXAMPLE F

Comparative—Outside Range—Oxidation

This example describes a method of catalyst preparation where alumina (30 g), prepared by heating a large crystallite pseudoboehmite to give a surface area of 230 m²/g is dried in a nitrogen flow at 400° C. for 1 hour and then cooled to room temperature under nitrogen. Then, small pieces of metallic sodium (4.5 g) and alumina are placed in a 300 ml round bottomed flask equipped with a mechanically driven stir paddle. The mixture is heated under nitrogen to 150° C., and at the point metallic sodium starts to melt, stirring is started. The mixture is stirred for 150 min at 150° C. The mixture is treated with 5% $O_2$ in $N_2$ is added at 126 ml/min until the ratio of $O_2$/Na is 0.15/1.

EXAMPLE G

Invention—Inside Range—Starting Material

This example describes one method of catalyst preparation. First, alumina (30 g) with a surface area of 250 m²/g, prepared by heating of a small crystallite pseudoboehmite alumina, is dried in a nitrogen flow at 400° C. for 1 hour and then cooled to room temperature under nitrogen. Then, small pieces of metallic sodium (4.5 g) and alumina are placed in a 300 ml round bottomed flask equipped with a mechanically driven stir paddle. The mixture is heated under nitrogen to 150° C., and at the point metallic sodium starts to melt, stirring is started. The mixture is stirred for 30 minutes in order to disperse the sodium onto the alumina. The mixture is then heat soaked at 150° C. for 2 hours with stirring. The mixture was then treated with 5% $O_2$ in $N_2$ at a 0.126 1/min rate until the $O_2$/Na ratio is 0.2/1.

EXAMPLE H

Comparative—Outside Range—Starting Material

This example describes a catalyst prepared according to Example G except that the alumina has a 200 m²/g surface area and is prepared by heating of a small crystallite pseudoboehmite alumina.

EXAMPLE I

Comparative—Outside Range—Starting Material

This example describes a catalyst prepared according to Example G except that the alumina has a 150 m²/g surface area and is prepared by heating of a small crystallite pseudoboehmite alumina.

EXAMPLE J

Comparative—Outside Range—Starting Material

This example describes a catalyst according to Example G except that the alumina has a 156 m²/g surface area and is prepared by heating of a gibbsite alumina.

EXAMPLE V-1

Table 5.1 shows results when catalysts (0.25 g) from Examples A–C, and E were reacted with high purity VNB (25 g) containing 70 wppm tetrahydroindene (THI) as major impurity at room temperature for 1 hour. All of these catalysts were on an alumina prepared from a large crystalline pseudoboehmite.

TABLE 5.1

| Experiments Number | Catalyst Example | Example Type | Conversion VNB to ENB (%) |
|---|---|---|---|
| 1 | A | Comparative | 55 |
| 2 | B | Invention | 99.6 |
| 3 | C | Invention | 99.6 |
| 4 | E | Comparative | 20 |

Experiments 2 and 3 illustrate that the activity of catalyst prepared by the method of this invention is not hindered by the presence of the THI impurity.

EXAMPLE V-2

Table 5.2 shows results from a series of experiments where VNB containing cyclopentadiene (CPD) impurity was isomerized to ENB with catalysts prepared in Examples A–C, and E. With catalysts A–C, CPD was completely removed from the reaction mixture by action of the catalyst to give high purity ENB. With catalyst E, about 10 wppm CPD remained in the reaction product.

Experiments 5–7 show the poisoning effect of CPD on the catalyst since the amount of catalyst must be increased to maintain constant conversion as the CPD concentration is increased. A comparison of Experiments 2 and 5 show that the invention catalyst is unaffected by 100 wppm CPD. However, catalyst A without oxygen activation is affected by as little as 20 wppm CPD (compare experiments 1 and 9). Catalyst E prepared with an alumina outside the surface area range of the preferred embodiment, is ineffective as a catalyst when the VNB contains 80 wppm CPD.

TABLE 5.2

| Exp. Number | Catalyst Example | Example Type | Catalyst Loading (wt %) | Starting CPD (wppm) | Conversion VNB to ENB (%) |
|---|---|---|---|---|---|
| 5 | B | Invention | 1.0 | 100 | 99.5 |
| 6 | B | Invention | 1.2 | 210 | 99.5 |
| 7 | B | Invention | 1.5 | 280 | 99.5 |
| 8 | C | Invention | 1.0 | 20 | 99.6 |
| 9 | A | Comparative | 1.0 | 20 | 45 |
| 10 | E | Comparative | 1.0 | 80 | 0 |

EXAMPLE V-3

Table 5.3 shows results from a series of experiments where VNB containing 4, 7, 8, 9-tetrahydroindene (THI) impurity was isomerized to ENB with catalysts prepared in Examples A and B at room temperature. In each case, the THI was converted to a mixture of indan, other THI isomers, and indene (which is removed by the catalyst) to give high purity ENB. THI did not act as a catalyst poison except at high levels as shown in Experiments 13 and 14. The THI is converted by the catalyst and some is removed by the catalyst to give higher purity ENB product. A comparison of catalysts A and B in experiments 1, 2, 13, and 14 show that the preferred catalyst is more resistant to poisoning at high THI levels than catalyst that is not activated with oxygen.

TABLE 5.3

| Exp. No. | Catalyst Example | Example Type | Catalyst Loading (wt %) | Starting THI (wppm) | Conversion VNB to ENB (%) | Isomerized THI formed (wppm) | Indan Formed (wppm) |
|---|---|---|---|---|---|---|---|
| 2 | B | Invention | 1.0 | 70 | 99.6 | 18 | 38 |
| 1 | A | Comparative | 4.1 | 70 | 99.6 | 18 | 38 |
| 11 | B | Invention | 0.9 | 220 | 99.5 | 58 | 118 |
| 12 | B | Invention | 0.9 | 350 | 99.5 | 100 | 200 |
| 13 | B | Invention | 1.5 | 2320 | 98 | 280 | 1080 |
| 14 | A | Comparative | 4.1 | 2320 | 74 | 60 | 870 |

EXAMPLE V-4

Table 5.4 shows results from a series of experiments where VNB containing 1,5-cyclooctadiene (COD) impurity was isomerized to ENB with catalysts prepared in Examples A and B at room temperature. In each case, the COD was quantitatively converted to 1,3-cyclooctadiene to give high purity ENB. COD did not act as a catalyst poison except at the high levels shown in experiments 18 and 19. When corrected for the different amounts of catalyst, the effect of high COD levels on catalyst A was greater than for the preferred catalyst B.

TABLE 5.4

| Experiment Number | Catalyst Example | Example Type | Catalyst Loading (wt %) | Starting COD (wppm) | Conversion VNB to ENB (%) |
|---|---|---|---|---|---|
| 15 | B | Invention | 1.0 | 20 | 99.6 |
| 16 | A | Comparative | 2.0 | 20 | 97 |
| 17 | B | Invention | 1.0 | 800 | 99.6 |
| 18 | A | Comparative | 2.0 | 2970 | 91 |
| 19 | B | Invention | 1.0 | 2970 | 91 |

EXAMPLE V-5

Table 5.5 shows results from a series of experiments where VNB containing vinylacteylene/CPD adducts (VNBD) impurity was isomerized to ENB with catalysts prepared in Examples A–D, F and G. The VNB also contained as impurities 600 wppm THI, 100 wppm COD, 5 wppm 0 as VNB-hydroperoxide. Hydroperoxides are catalyst poisons because of the acidity of the —$O_2H$ function, and the effect on catalyst at the level in this feed would be equivalent to the poisoning effect of 160 wppm CPD. The COD and THI impurities will not act as catalyst poisons at these levels in the VNB.

VNBD is a mixture of 5-vinyl-2,5-norbornadiene and 5-ethynyl-2-norbornene that is formed in the reaction of vinylacetylene impurity with butadiene during VNB synthesis. In each case, the VNBD was completely removed from the reaction mixture by action of the catalyst to give high purity ENB. The experiments clearly show that the preferred catalysts B, C, and G have higher poison resistance.

TABLE 5.5

| Experiment Number | Catalyst Example | Example Type | Catalyst Loading (wt %) | Starting VNBD (wppm) | Conversion VNB to ENB (%) |
|---|---|---|---|---|---|
| 20 | B | Invention | 1.4 | 700 | 99.6 |
| 21 | D | Comparative | 1.0 | 700 | 60 |
| 22 | A | Invention | 1.4 | 700 | 66 |

TABLE 5.5-continued

| Experiment Number | Catalyst Example | Example Type | Catalyst Loading (wt %) | Starting VNBD (wppm) | Conversion VNB to ENB (%) |
|---|---|---|---|---|---|
| 23 | C | Invention | 1.4 | 700 | 96 |
| 24 | F | Comparative | 1.4 | 700 | 60 |
| 25 | G | Invention | 1.0 | 700 | 99.6 |

EXAMPLE V-6

This example shows the effect of alumina surface area on catalyst activity when the starting alumina is prepared from a small crystallite pseudoboehmite alumina when using the high purity VNB from Example I.

TABLE 5.6

| Experiment Number | Catalyst Example | Example Type | Surface Area ($m^2/g$) | Activity No. |
|---|---|---|---|---|
| 26 | G | Invention | 250 | 550 |
| 27 | H | Comparative | 200 | 250 |
| 28 | I | Comparative | 150 | 120 |

EXAMPLE V-7

This example shows the effect of alumina surface area on catalyst activity when the starting alumina is prepared from a large crystallite pseudoboehmite alumina compared to the activity of a catalyst when the alumina support is prepared by heating of a gibbsite alumina. A comparison of this data with the data in the table below show that high activity catalyst can not be prepared from gibbsite alumina in any surface area range. Note that these results were much better than those in FIG. 1 due to the more optimum oxidation and heat treating conditions.

TABLE 5.7

| Experiment Number | Catalyst Example | Example Type | Alumina Precursor | Surface Area ($M^2/G$) | Activity Number |
|---|---|---|---|---|---|
| 28 | C | Invention | Large Pseudoboehmite | 167 | 550 |
| 29 | J | Comparative | Gibbsite | 158 | 130 |

EXAMPLE V-8

This example shows the isomerization of VNB to give high quality ENB in the presence of greater than 0.5 wt. % vinylcyclohexene (VCH). The vinylcyclohexene is converted to ethylbenene which is an inert diluent in the process to prepare EPDM rubber from the ENB. This isomerization reaction is run under negative pressure or swept with nitrogen to remove hydrogen evolved during conversion of the VCH to ethylbenzene.

A mixture containing 70 wt. % VNB and 30 wt % VCH is mixed with 2.7 wt. % catalyst of Example C at 70° C. After 2 hours, the mixture was analyzed by gas chromatography. The conversion of VNB to ENB was 99.5% and the conversion of VCH to ethylbenzene was 99.9%. This is a suitable feed to an EPDM manufacturing plant.

The examples set forth above illustrate aspects of the invention and are not limitations on the scope of the invention which is set forth in the claims below. Many other variations and modifications may be made to the process and catalyst described above without departing from the concept of the present invention. Accordingly, it should be clearly understood that the methods referred to in the foregoing description are illustrative only and are not intended as limitations on the scope of the invention.

We claim:

1. An activated isomerization catalyst prepared by:
   providing a substantially dry support material consisting essentially of an alumina prepared from a starting material consisting essentially of a pseudoboehmite wherein said alumina has a surface area selected from the group consisting of in the range of from about 125 $m^2/g$ to about 195 $m^2/g$ when prepared from a starting material consisting of a first pseudoboehmite having an average crystallite size substantially the same as to a catapal grade pseudoboehmite or wherein said alumina has a surface area in the range of from about 220 $m^2/g$ to about 280 $m^2/g$ when prepared from a starting material of a second pseudoboehmite having an average a crystallite size smaller than a catapal grade pseudoboehmite;
   mixing a metallic form alkali metal and the substantially dry support material under conditions comprising a time and an elevated temperature effective to ensure substantially complete thermal mixing and to produce a catalyst precursor mixture comprising a substantially uniform dispersion of the alkali metal on the support;
   activating the catalyst precursor mixture by treatment with an oxygen-containing gas under conditions effective to produce an activated catalyst which maintains a higher rate of activity during isomerization than said catalyst maintains in the absence of said treatment with said oxygen-containing gas.

2. An activated isomerization catalyst prepared by:
   providing a substantially dry support material consisting essentially of an alumina prepared from a starting material consisting essentially of a pseudoboehmite wherein said alumina has a surface area selected from the group consisting of in the range of from about 125 $m^2/g$ to about 195 $m^2/g$ when prepared from a starting material consisting of a first pseudoboehmite having an average crystallite size substantially the same as a catapal grade pseudoboehmite or wherein said alumina has a surface area in the range of from about 230 $m^2/g$ to about 260 $m^2/g$ when prepared from a starting material of a second pseudoboehmite having an average a crystallite size smaller than a catapal grade pseudoboehmite;
   mixing a metallic form of an alkali metal and the substantially dry support material under conditions comprising a time and an elevated temperature effective to ensure substantially complete thermal mixing and to produce a catalyst precursor mixture comprising a substantially uniform dispersion of the alkali metal on the support;
   activating the catalyst precursor mixture by treatment with an oxygen-containing gas under conditions effective to produce an activated catalyst which maintains a higher rate of activity during isomerization than said catalyst maintains in the absence of said treatment with said oxygen-containing gas.

3. An activated isomerization catalyst in accordance with claim 1, wherein said alumina has a surface area of 140 to 180 $m^2/g$ when prepared from a starting material consisting of a second crystallite pseudoboehmite.

4. An activated isomerization catalyst in accordance with claim 1, wherein said alkali metal is selected from the group consisting of lithium, sodium, potassium, cesium, rubidium, and mixtures thereof.

5. An activated isomerization catalyst in accordance with claim 4, wherein the alkali metal is sodium.

6. An activated isomerization catalyst in accordance with claim 5, wherein the temperature at which the sodium is dispersed on the dry support material in step (b) is from about 100° C. to 300° C.

7. An activated isomerization catalyst in accordance with claim 1, wherein the contact between said catalyst precursor mixture and said oxygen-containing gas in step (d) occurs at a temperature of 100° C. to 250° C.

8. An activated isomerization catalyst in accordance with claim 7, wherein the ratio of total moles of activating oxygen to total atoms of alkali metal in step (d) is in the range of 0.005:1 to 1:1.

9. An activated isomerization catalyst in accordance with claim 8, wherein the ratio of total moles of activating oxygen to total atoms of alkali metal in step (d) is in the range of 0.05:1 to 0.2:1.

10. An activated isomerization catalyst in accordance with claim 7, wherein said oxygen-containing gas comprises nitrogen and from about 2 to 10 mole percent oxygen.

11. An activated isomerization catalyst in accordance with claim 1, wherein the activity number is greater than 50.

12. An activated isomerization catalyst in accordance with claim 11, wherein the activity number is greater than 100.

13. An activated isomerization catalyst in accordance with claim 12, wherein the activity number is greater than 150.

14. A process for preparing a high quality olefin comprising catalytically isomerizing a stream comprising an olefin which comprises contacting the stream comprising an olefin with an activated catalyst, wherein the activated catalyst is prepared in accordance with claim 1.

15. A process in accordance with claim 14, wherein the stream comprising an olefin further comprises one or more reactive impurities.

16. A process in accordance with claim 15, wherein said reactive impurities are selected from the group consisting of other mono olefins, acidic oxygenates, and diene impurities.

17. A process in accordance with claim 16, wherein said diene impurities are selected from the group consisting of cyclopentadiene, cyclooctadiene, tetraahydroindene, vinylnorbornadiene, ethynyinorborene, hydroperoxides, vinylcyclohexenes, and methyl vinylcyclohexenes.

18. A process in accordance with claim 14, wherein said olefin is alkenyl bridged compound.

19. A process in accordance with claim 18, wherein said alkenyl bridged ring compound is 5-vinyl-2-norbornene.

20. A process in accordance with claim 19, wherein said olefin is 5-vinyl-2-norbornene.

21. A process in accordance with claim 14, wherein the contact between the stream comprising an olefin and the activated catalyst occurs at a temperature from about 20° to about 100° C.

22. The catalyst of claim 1 wherein said alumina has a surface area in the range of from about 140 $m^2/g$ to about 180 $m^2/g$ when prepared from a starting material of a said first pseudoboehmite.

23. The catalyst of claim 1 wherein said alumina has a surface area in the range of from about 150 $m^2/g$ to about 180 $m^2/g$ when prepared from a starting material of a said first pseudoboehmite.

24. The catalyst of claim 1 wherein said alumina has a surface area in the range of from about 230 $m^2/g$ to about 270 $m^2/g$ when prepared from a starting material of a said second pseudoboehmite.

25. The catalyst of claim 1 wherein said alumina has a surface area of about 250 $m^2/g$ when prepared from a starting material of a said second pseudoboehmite.

26. An activated isomerization catalyst prepared by:

providing a substantially dry support material consisting essentially of an alumina prepared from a starting material consisting essentially of a pseudoboehmite wherein said alumina has a surface area selected from the group consisting of in the range of from about 125 $m^2/g$ to about 195 $m^2/g$ when prepared from a starting material consisting of a first pseudoboehmite having an average crystallite size substantially the same as a catapal grade pseudoboehmite or wherein said alumina has a surface area in the range of from about 220 $m^2/g$ to about 280 $m^2/g$ when prepared from a starting material of a second pseudoboehmite having an average a crystallite size smaller than a catapal grade pseudoboehmite;

mixing a metallic form of an alkali metal comprising sodium and the substantially dry support material under conditions comprising a time and an elevated temperature effective to ensure substantially complete thermal mixing and to produce a catalyst precursor mixture comprising a substantially uniform dispersion of the alkali metal on the support;

activating the catalyst precursor mixture by treatment with an oxygen-containing gas under conditions effective to produce an activated catalyst which maintains a higher rate of activity during isomerization than said catalyst maintains in the absence of said treatment with said oxygen-containing gas.

* * * * *